United States Patent

Hino et al.

[11] Patent Number: 5,814,681
[45] Date of Patent: Sep. 29, 1998

[54] RESTORATIVE COMPOSITION FOR HARD TISSUE AND DISPENSING APPARATUS THEREFOR

[75] Inventors: Kenichi Hino; Toshihide Nakashima, both of Kurashiki, Japan

[73] Assignee: Kuraray Co., Ltd., Kurashiki, Japan

[21] Appl. No.: 652,599

[22] PCT Filed: Oct. 13, 1995

[86] PCT No.: PCT/JP95/02110

§ 371 Date: Jun. 13, 1996

§ 102(e) Date: Jun. 13, 1996

[87] PCT Pub. No.: WO96/11715

PCT Pub. Date: Apr. 25, 1996

[30] Foreign Application Priority Data

Oct. 13, 1994 [JP] Japan .................................. 6-247942

[51] Int. Cl.$^6$ .............................. A61L 25/00; A61K 6/08; C08K 3/32
[52] U.S. Cl. ......................... 523/113; 523/115; 523/116; 524/264; 524/417; 604/191; 604/416; 222/145.5; 222/145.6
[58] Field of Search .................................. 523/115, 116, 523/113; 524/417, 264; 604/191, 416; 222/145.5, 145.6

[56] References Cited

U.S. PATENT DOCUMENTS

| 4,380,432 | 4/1983 | Orlowski et al. | 523/118 |
| 5,033,650 | 7/1991 | Colin et al. | 433/90 |
| 5,430,074 | 7/1995 | Barnes et al. | 433/228.1 |

FOREIGN PATENT DOCUMENTS

90/04952  5/1990  WIPO ...................... 433/90

*Primary Examiner*—Andrew E. C. Merriam
*Attorney, Agent, or Firm*—Oblon, Spivak, McClelland, Maier & Neustadt, P.C.

[57] ABSTRACT

A restorative composition for hard tissue, comprising a paste (A) containing an inorganic calcium phosphate powder, a polymerizable monomer mixture and a polymerization initiator, and a paste (B) containing an inorganic calcium phosphate powder, a polymerizable monomer mixture and a polymerization accelerator, wherein the content of the inorganic calcium phosphate powder in each paste is 75–85% by weight, and each monomer mixture contains a monomer of the formula (1):

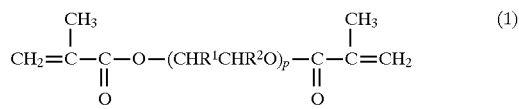

and a monomer of the formula (2):

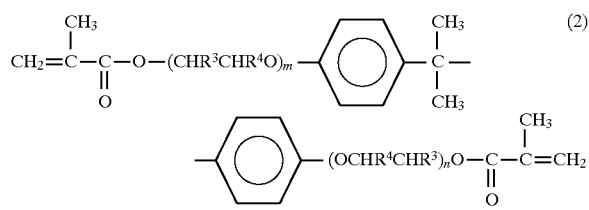

the content of the monomer (1) accounting for 40–65% by weight of the monomer mixture as a whole. The composition can well adhere to the bone and has a sufficient water resistance. As it generates little heat upon hardening, it is less detrimental to the patient's tissues. Furthermore, the paste has an appropriate consistency, which facilitates homogeneous mixing of the paste and application of the resultant mixture to the affected part by the use of a dispensing apparatus. Thus, the restorative composition can be used not only as a bone cement but also as a filler for the defected part of the bone, a bone prosthesis or an artificial bone.

3 Claims, 2 Drawing Sheets

RESTORATIVE COMPOSITION FOR HARD TISSUE AND DISPENSING APPARATUS THEREFOR

TECHNICAL FIELD

The present invention relates to a restorative composition for hard tissue, which is used as a bone cement, a bone prosthesis, an artificial bone, and the like, and to a method for dispensing the restorative composition for hard tissue.

BACKGROUND ART

A bone cement comprising a powder agent containing polymethyl methacrylate and benzoyl peroxide (polymerization initiator), and a liquid agent containing methyl methacrylate and a tertiary amine such as N,N-dimethyl-p-toluidine (accelerator) has been conventionally used for fixing artificial joints. This bone cement is prepared immediately before fixing artificial joints during operation by mixing the powder agent and the liquid agent. The obtained mixture is applied to the affected part by a dispenser called a cement gun and allowed to cure. Such bone cement is associated with problems in that ① the toxicity of methyl methacrylate causes vasodepression in patients undergoing operation, ② the heat generated during polymerization could give damages to the tissues of the patients, ③ the fixed artificial joints could get loose with time due to the failure in adhering polymethyl methacrylate to hard tissues, ④ the mixing of the powder agent and the liquid agent just before use makes bad smell of polymethyl methacrylate fill the operation room and gives detrimental effect ⑤ slow mixing of the powder agent and the liquid agent leads to initiation of curing of the mixture, thereby making the mixture unavailable as a bone cement, and ⑥ insufficient mixing of the powder agent and the liquid agent results in too low a strength of the cured material, so that the artificial joints cannot be firmly fixed with hard tissues.

In an attempt to improve the biocompatibility of bone cements, Japanese Patent Examined Publication No. 42384/1979 has proposed a bone cement comprising a composition containing polymethyl methacrylate and methyl methacrylate, and bioactive glass having an apatite crystal phase superior in biocompatibility, and Japanese Patent Application under PCT laid-open under Kohyo No. 503148/1987 has proposed a bone cement comprising di(meth) acrylate and inorganic filler particles which are at least partially absorbed by the bone.

The above-mentioned bone cements are characterized by the use of a biocompatible filler, and the latter is particularly advantageous in that it does not contain methyl methacrylate which is problematic in terms of toxicity and adhesive strength. These bone cements may provide favorable results in terms of biocompatibility, whereas are not necessarily satisfactory in terms of operability.

Speaking from the aspect of operability, quick and thorough mixing is required to simultaneously solve the above-mentioned problems ⑤ and ⑥ which may seem inconsistent. In addition, the bone cement is required to have an adequate flowability before curing to facilitate filling into the affected part.

A practical bone cement should afford sufficient adhesive strength between the cured material and hard tissues, and the cured material should have sufficient water resistance permitting retention of suitable strength in the body for an extended period of time.

The present invention aims at providing a restorative composition for hard tissue, which is capable of exhibiting the above-mentioned properties requested as a practical bone cement, and which is superior in biocompatibility and operability.

The present invention also aims at providing a method for dispensing such restorative composition for hard tissue.

DISCLOSURE OF THE INVENTION

The present inventors have found that a restorative composition for hard tissue comprising a paste obtained by mixing, at a certain ratio, an inorganic calcium phosphate powder superior in biocompatibility and adhesion to bone, and a polymerizable monomer capable of imparting sufficient mechanical strength and water resistance to the cured material meets the aforementioned objects of the present invention, and further studies resulted in the completion of the present invention.

Accordingly, the present invention provides a restorative composition for hard tissue, comprising a paste (A) containing an inorganic calcium phosphate powder (hereinafter to be briefly referred to as inorganic powder), a polymerizable monomer mixture (hereinafter briefly referred to as monomer mixture) and a polymerization initiator, and a paste (B) containing an inorganic powder, a monomer mixture and a polymerization accelerator, wherein the content of the inorganic powder in each paste is 75–85% by weight, and the above-mentioned polymerizable monomer mixtures each contain a monomer of the formula (1):

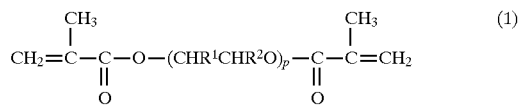

wherein $R^1$ and $R^2$ may be the same or different and each is a hydrogen atom or a methyl, and p is an integer of 1–4, and a monomer of the formula (2):

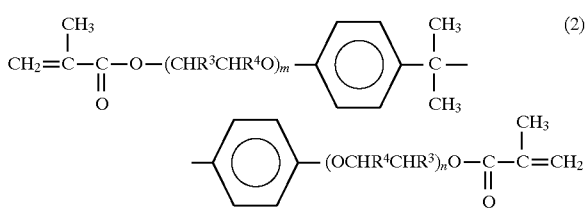

wherein $R^3$ and $R^4$ may be the same or different and each is a hydrogen atom or a methyl, m and n are each an integer of 1–5, and m+n is 2–6, the monomer of formula (1) being contained in a proportion of 40–65% by weight based on the total weight of the monomer mixtures.

The present invention also provides a method for dispensing the above-mentioned restorative composition for hard tissue.

As used herein, the term "hard tissue" denotes hard tissues in living organisms, such as bones, cartilages, joints and teeth.

As used herein, "being superior in operability" means that the respective pastes (A) and (B) constituting the restorative composition for hard tissue have adequate flowability or consistency.

The consistency of the paste is expressed by the diameter (mm) of a shape formed by a certain amount of the paste which was interposed between two glass plates and applied with a certain pressure for a predetermined time. The preferable consistency of the paste when 0.5 ml of the paste is applied with a 40 g pressure at 25° C. for 30 seconds is expressed by a diameter of not less than 20 mm and not more than 27 mm.

When the consistency of the paste falls within such range, the paste can be mixed homogeneously, and the obtained restorative composition for hard tissue has suitable flowability which desirably permits easy application of the composition to the affected part. In particular, the use of the dispenser to be mentioned later enables simultaneous operation of the above-mentioned mixing and filling.

The flowability of the paste is quantitatively defined by the force necessary for extruding, at a predetermined rate, a certain amount of paste filled in a container having a certain shape. To be specific, the material is filled in a cylinder having an inner diameter of 13 mm and delivery end diameter of 3.5 mm, and a piston placed in the cylinder is pressed thereinto at 5 mm/min at 25° C. The flowability is expressed by the force required to press the piston deeper in. The paste having a suitable flowability preferably requires an extrusion force of not more than 2N, more preferably not more than 1N. When the paste has a flowability falling within the above-mentioned range, the force necessary for the above-mentioned mixing and filling operation can be small enough to enable performing such operation easily with one hand.

A paste having too high a flowability drips from a dispenser and flows out from the application site, while a paste having too low a flowability is associated with difficulty in being extruded from a dispenser, so that it cannot be sufficiently injected into the application site. Either instance is inconvenient for operation.

The inorganic powder to be used in the present invention is exemplified by calcium secondary phosphate, octacalcium phosphate, α-tricalcium phosphate, β-tricalcium phosphate, tetracalcium phosphate and hydroxyapatite, with preference given to α-tricalcium phosphate, β-tricalcium phosphate and hydroxyapatite in view of superior biocompatibility.

In the present invention, the inorganic powder content of the respective pastes (A) and (B) should be 75–85% by weight.

When the inorganic powder content of the respective pastes is less than 75% by weight, various defects are caused. For example, greater part of the surface of the inorganic powder is covered with polymer, so that the adhesion to bone is prevented and biocompatibility becomes poor; when the restorative composition for hard tissue is cured, polymerization generates greater heat with the likelihood of giving damages to the patient's tissues; and the strength of the cured material becomes insufficient. On the other hand, when the inorganic powder content of the respective pastes exceeds 85% by weight, the flowability of the paste becomes low, and in some cases, a homogeneous restorative composition cannot be obtained, which in turn results in failure to realize the objective superior operability of the present invention.

It is preferable that the components of the inorganic powder in paste (A) and contents thereof, and those in paste (B) be the same.

The inorganic powder to be used in the present invention preferably has a particle size of 0.1–100 μm, more preferably 0.1–50 μm. Such wide distribution of particle size of the inorganic powder enables increase of the inorganic powder content of the paste.

The inorganic powder is preferably compact. The term "compact" here means that the powder does not substantially have voids, and such powder is exemplified by those wherein the volume of fine voids as measured by the mercury intrusion method is not more than 0.1 ml/g. When the inorganic powder having the volume of fine voids which falls within said range is used, a monomer mixture to be mixed with the inorganic powder is not absorbed into the voids in the inorganic powder, and a restorative composition having the above-mentioned high inorganic powder content can be obtained.

For a stable restorative composition to be obtained by mixing an inorganic calcium phosphate powder and an organic monomer mixture, it is preferable to introduce an organic group onto the surface of the inorganic powder. For this end, a treatment with an organic silane coupling agent may be performed. Specifically, an inorganic powder is subjected to a primary treatment with an organic silane coupling agent, a heat-treatment, and then a secondary treatment with an organic silane coupling agent, whereby a restorative composition having a suitable flowability can be obtained and the strength of the cured material can be improved. This is considered to be attributable to the treatment with an organic silane coupling agent and heat treatment applied to the silicon-free inorganic calcium phosphate powder, thereby introducing silicon onto the surface of the inorganic powder, which silicon is then bound with the second organic silane molecule.

The organic silane coupling agent is exemplified by γ-methacryloxypropyltrimethoxysilane, γ-methacryloxypropyltriethoxysilane, γ-methacryloxypropyl-tris(β-methoxyethoxy)silane and γ-aminopropyltriethoxysilane. While the silane coupling agent to be used for the two organic silane treatments may be the same or different, a silane coupling agent having polymerizable double bond, such as γ-methacryloxypropyltrimethoxysilane, is preferably used for the second treatment to provide stronger bond with the cured material. The heat treatment to be performed in between the two silane treatments may be performed at a temperature at which the organic silane coupling agent introduced by the first silane treatment can be thermally decomposed. Inasmuch as a high temperature may affect the composition and structure of the inorganic powder, the desirable temperature of the heat treatment is 300° C.–800° C.

The monomer mixture to be used in the present invention contains a monomer of the formula (1):

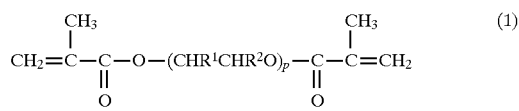

wherein $R^1$ and $R^2$ may be the same or different and each is a hydrogen atom or a methyl, and p is an integer of 1–4, and a monomer of the formula (2):

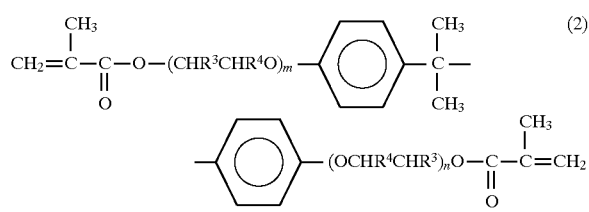

wherein $R^3$ and $R^4$ may be the same or different and each is a hydrogen atom or a methyl, m and n are each an integer of 1–5, and m+n is 2–6.

The monomer of the formula (1) is a highly flowable liquid and is required for dissolving other monomers and for forming a stable restorative composition by homogeneously mixing with an inorganic powder. This monomer is hydrophilic and remains in a trace amount on the surface of the cured material due to the polymerization inhibitory action of the surrounding oxygen. This residual monomer is considered to dissolve in surrounding water, whereby particles of inorganic powder having affinity for hard tissue come into direct contact with the surrounding hard tissue, and bind therewith to strengthen the adhesion to the hard tissue.

FIG. 1 is a surface scanning electron microphotograph of a plate-shaped cured material formed from the restorative composition (composition of Example 1 to be described later) of the present invention. As is evident from this photograph, the surface of the cured material formed from the restorative composition of the present invention exposes inorganic particles. In contrast, FIG. 2 is a surface scanning electron microphotograph of a cured material obtained from the composition (composition of Comparative Example 3 to be described later) disclosed in EP-B-123323. This composition does not comprise a monomer of the formula (1) which is an essential element in the present invention. Therefore, the inorganic particles on the surface of the cured material are covered with polymer, and cannot directly adhere to the hard tissue in the body. In consequence, such composition is considered to be inferior to the composition of the present invention in the adhesion of the cured material to the hard tissue.

Examples of the monomer (1) of the formula (1) include ethyleneglycol dimethacrylate, diethyleneglycol dimethacrylate, triethyleneglycol dimethacrylate and propyleneglycol dimethacrylate, with preference given to triethyleneglycol dimethacrylate.

The monomer of the formula (2) is a liquid having low flowability and is required for retaining the inorganic powder to form a stable restorative composition. This monomer is hydrophobic and is also required for improving the water resistance of the cured material.

Examples of the monomer (2) include 2,2-bis(4-methacryloxyethoxyphenyl)propane, 2,2-bis(4-methacryloxypolyethoxyphenyl)propane, 2,2-bis(4-methacryloxypolypropoxyphenyl)propane, with preference given to 2,2-bis(4-methacryloxyethoxyphenyl)propane.

It is the composition of the monomer mixture that is important in the present invention to achieve superior operability. That is, the content of the monomer of the formula (1) should be 40–65% by weight, preferably 45–60% by weight, of the total weight of the monomer mixtures. When the content of the monomer of the formula (1) is beyond 65% by weight of the total weight of the monomer mixtures, the obtained paste shows poor stability, allowing separation of the inorganic powder from the paste. On the other hand, when the content of the monomer of the formula (1) is less than 40% by weight of the total weight of the monomer mixtures, the flowability of the paste becomes too low to realize the objective superior operability of the present invention.

The monomer of the formula (2) is added such that the total of the monomer of the formula (1) and that of the formula (2) and the third component to be described later becomes 100% by weight.

The above-mentioned monomer mixture may contain a third component such as hydrophobic dimethacrylate (e.g., 2,2-bis(4-(3-methacryloxy-2-hydroxypropoxy)phenyl)propane (hereinafter abbreviated as Bis-GMA) and 2,2-bis(4-methacryloxyphenyl)propane). The hydrophobicity here means that the saturation solubility in physiological saline at 37° C. is not more than 500 ppm.

Such hydrophobic dimethacrylate is used in an amount corresponding to 0–30% by weight of the total monomer mixtures.

The monomer mixture constituting paste (A) and the monomer mixture constituting paste (B) preferably have the same composition.

The polymerization initiator or polymerization accelerator to be used in the present invention when added alone does not initiate polymerization at normal temperature in a short time. By mixing them, however, radicals are produced which function to cure the monomer mixture.

Examples of the polymerization initiator include organic peroxides such as diacyl peroxides and peroxy esters. Specific examples thereof include benzoyl peroxide, 2,4-dichlorobenzoyl peroxide, m-tolyl peroxide, t-butyl peroxybenzoate, di-t-butyl peroxyisophthalate, 2,5-dimethyl-2,5-di(benzoylperoxy)hexane, 2,5-dimethyl-2,5-di((o-benzoyl)-benzoylperoxy)hexane and 2,5-dimethyl-2,5-di((o-benzoyl)-benzoylperoxy)hexine-3,3,3',4,4'-tetra(t-butylperoxycarbonyl)benzophenone.

The polymerization accelerator is preferably a tertiary amine having amino group directly bonded to the aromatic ring, which is exemplified by N, N-dimethyl-p-toluidine, N,N-dimethylaniline, N-methyl-N-(2-hydroxyethyl)aniline, N,N-di(2-hydroxyethyl)aniline, N,N-di(2-hydroxyethyl)-p-toluidine, N,N-di(2-hydroxypropyl)aniline and N,N-di(2-hydroxypropyl)-p-toluidine.

These polymerization initiator and polymerization accelerator need to be used in an amount enough to sufficiently cure the monomer mixture, which is generally 0.1–2% by weight relative to the monomer mixture, for the both.

When the both pastes are mixed in the present invention, the surface of the mixture is sometimes slow in curing due to the oxygen in the air. To prevent this, a light polymerization initiator may be further added to the paste, by which curing may be effected also from the surface upon irradiation of the light, which is particularly effective in the case of a bone cement for fixing artificial joints in that the fixing takes only a short time. Such light polymerization initiator may be a combination of camphor quinone and amines.

The restorative composition for hard tissue of the present invention is preferably sterilized, which may be achieved by separately sterilizing the monomer mixture and inorganic powder, and mixing them to give a paste. Alternatively, sterilization may be applied after forming the paste. The method for sterilization can be appropriately selected from known methods such as EOG sterilization and filtration.

While the mixing ratio of paste (A) and paste (B) is not particularly limited, it is preferably 1:10–10:1, most preferably 1:1 by volume.

The restorative composition for hard tissue of the present invention suffers from insufficient strength of the cured material unless paste (A) containing a polymerization initiator and paste (B) containing a polymerization accelerator are homogeneously mixed, whereas excess time for mixing leads to the initiation of curing before application of the mixture to the affected part, thereby making the mixture unavailable. In addition, air foams mixed therein could cause insufficient strength. Contamination of bacteria in the air during mixing and volatilization of the monomer vapor into the air should be prevented. The both pastes should be preserved in separate containers, since curing starts upon mixing, and are preferably mixed with ease when in use. Consequently, a supply apparatus comprising two containers to place both pastes in separately, extrusion mechanisms to deliver the pastes from the two containers, delivery holes in said containers, and a static mixer mechanism to lead and homogeneously mix the both pastes delivered from said delivery holes is most suitably used for the object of the present invention.

A preferable method is the use of a static mixer described in a literature [S. D. Cheng et al., Static Mixing Handbook-Everything about Static Mixing Process, *Sogo Kagaku Kenkyusho*, pp. 9–15 (1973)]. The use of this apparatus enables homogeneous mixing of the two pastes (A) and (B), and sterile application of the obtained composition to the affected part in an efficient manner in a short time.

When the restorative composition for hard tissue is applied to the affected part using this static mixer, too low a flowability of the paste makes it difficult for the mixer to deliver the paste, and too high a flowability causes dripping of the paste from the tip of the mixer and defective shape-forming performance of the paste. Thus, the dispensing method of the present invention is characterized by the combination of a paste composition which affords appropriate consistency and a supply apparatus for homogeneously mixing the paste and injecting the paste composition into the affected part.

FIG. 3 shows one example of the apparatus to be used for mixing the pastes. The apparatus consists of a dispenser 1, a mixer 2, a pair of syringe 3 containing paste (A) and syringe 3' containing paste (B), and a plunger 4. When the trigger of the dispenser 1 is pulled, the plunger 4 is pressed deeper in and each paste in the syringes 3 and 3' is extruded through a common delivery hole 5 into the mixer 2. The mixer 2 has baffles to continuously perform separation and mixing. The pastes are thoroughly mixed while being carried through the mixer 2 and injected into the affected part directly from the outlet of the mixer 2 or via a tube having a desired length.

In view of the use of the apparatus upon direct contact with the tissues within the body of patients, it is desirable that the apparatus be sterilized. The method for sterilization can be appropriately selected from known methods such as EOG sterilization and autoclave sterilization. The mixer 2 and syringes 3 and 3' are desirably disposable.

Figure 1:
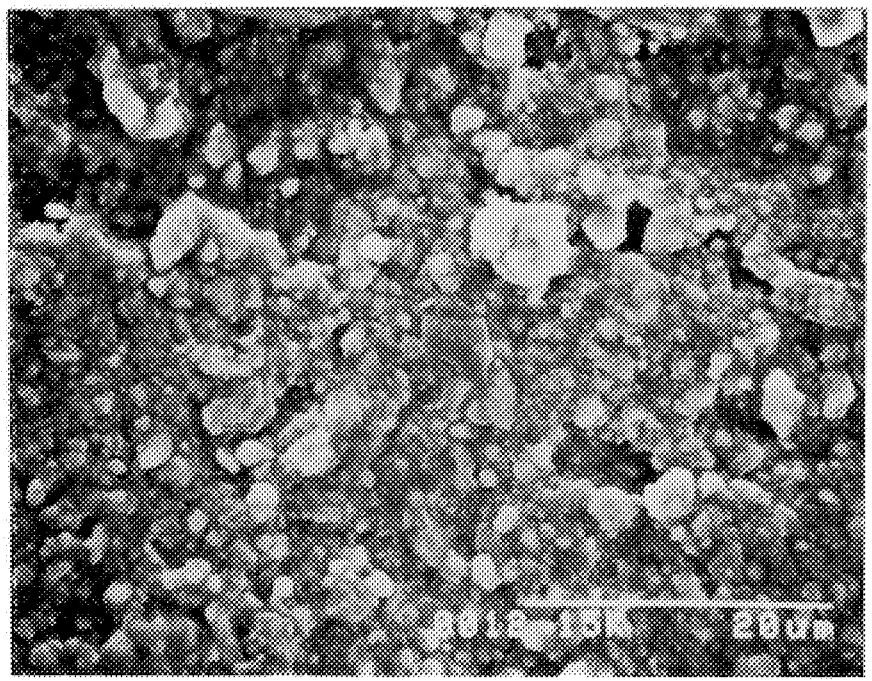
FIG. 1 is a surface electron microphotograph of a plate-shaped cured material obtained from the composition of Example 1.

The present invention is explained in the following by way of Examples, to which the present invention is not limited.

Reference Example 1 (production of hydroxyapatite powder)

According to the method described in the literature [E. Hayek and H. Newesel, "Inorganic Synthesis VII", McGraw-Hill, p. 63, New York (1963)], an aqueous solution of ammonium hydrogenphosphate, an aqueous solution of calcium nitrate and aqueous ammonia were mixed in a $Ca/PO_4$ molar ratio of 1.67 and heated to synthesize hydroxyapatite. The hydroxyapatite obtained was subjected to centrifugal dehydration, dried at 80° C., sintered at 1100° C. for 2 hours, and pulverized in a ball mill to give a hydroxyapatite powder having an average particle size of 4 μm, particle size 0.1–50 μm, density 3.27 g/ml and pore volume 0.057 ml/g.

The obtained hydroxyapatite powder (400 g) was added to a solution (240 ml) of γ-methacryloxypropyl trimethoxysilane (8 g) in acetone, and the mixture was stirred at room temperature for one hour. Acetone was distilled away under reduced pressure, and the residue was dried at room temperature and heated at 750° C. for 2 hours. Then, the obtained powder was added to a solution (600 ml) of γ-methacryloxypropyl trimethoxysilane (8 g) in toluene, which was followed by refluxing under heating for 3 hours. Toluene was distilled away under reduced pressure, and the residue was dried at room temperature.

Reference Example 2 (determination of the composition of polymerizable monomer mixture)

Triethylene glycol dimethacrylate (hereinafter to be abbreviated as TEGDMA) as the monomer of the formula (1), 2,2-bis(4-methacryloxyethoxyphenyl)propane (hereinafter to be abbreviated as Bis-MEPP) as the monomer of the formula (2), and Bis-GMA as the third component dimethacrylate were mixed in the weight ratio shown in Table 1, and benzoyl peroxide (0.3 part by weight) and hydroxyapatite powder (80 parts by weight) obtained in Reference Example 1 were added to this monomer mixture (20 parts by weight), which mixture was well admixed in a mortar to give a paste. The obtained paste was filled in a cylinder (inner diameter 13 mm, delivery end diameter 3.5 mm). The force necessary for pressing the piston placed in the cylinder thereinto at 5 mm/min was measured using Instron universal testing machine, the results of which are shown in Table 1.

TABLE 1

| monomer composition | 1 | 2 | 3 | 4 | 5 | 6 | 7 | 8 | 9 | 10 | 11 |
|---|---|---|---|---|---|---|---|---|---|---|---|
| TEGDMA* | 30 | 40 | 50 | 50 | 50 | 50 | 50 | 70 | 70 | 70 | 100 |
| Bis-MEPP* | 35 | 30 | 50 | 40 | 30 | 20 | 0 | 30 | 15 | 0 | 0 |
| Bis-GMA* | 35 | 30 | 0 | 10 | 20 | 30 | 50 | 0 | 15 | 30 | 0 |
| force (N) necessary for extrusion | 3.14 | 1.08 | 1.67 | 1.37 | 1.08 | 0.39 | 0.59 | — | — | — | — |

*parts by weight

In Table 1, "-" means sedimentation of hydroxyapatite powder. When the content of TEGDMA in the monomer mixture was not more than 25% by weight, the monomer mixture had low flowability, which in turn resulted in failure to homogeneously admix the monomer mixture and the hydroxyapatite powder.

As a result, it has been found that the TEGDMA content of the monomer mixture as a whole should be 40–65% by weight to afford a restorativecomposition for hard tissue, which has a superior operability requesting an extrusion force of not more than 2N.

EXAMPLE 1

(Preparation of paste)

TEGDMA (50 parts by weight), Bis-MEPP (20 parts by weight) and Bis-GMA (30 parts by weight) were mixed, and benzoyl peroxide (0.3 part by weight) and hydroxyapatite powder (80 parts by weight) obtained in Reference Example 1 were added to this monomer mixture (20 parts by weight), which mixture was well admixed in a mortar to give a paste (A1). Separately, a monomer mixture (20 parts by weight) same as above was admixed with N,N-di(2-hydroxypropyl)-p-toluidine (0.4 part by weight) and hydroxyapatite powder (80 parts by weight) to give a paste (B1).

(Evaluation of the water resistance of cured material)

Figure 3:
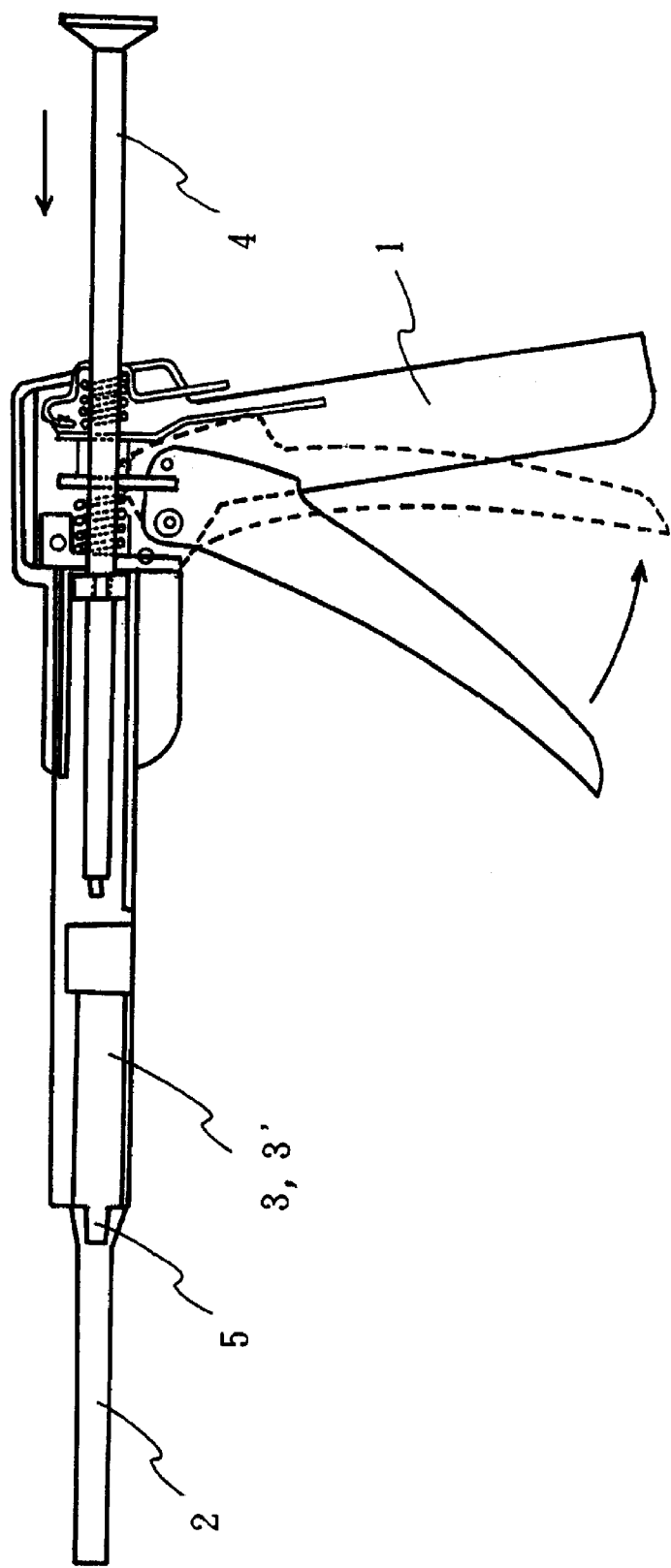
FIG. 3 is a schematic view (lengthwise cross section) of the apparatus to be used for mixing the pastes, wherein 1 is a dispenser, 2 is a mixer, 3 and 3' are syringes, and 4 is a plunger.

Equivalent amounts of the paste (A1) and paste (B1) obtained in the above were mixed in a dispenser shown in FIG. 3. The obtained composition was extruded in a Teflon tube and allowed to cure to give a round rod cured material having a diameter of 3 mm and a length of 25 mm.

The obtained cured material was immersed in physiological saline at 37° C. and preserved for a certain time. The cured material was weighed before and after the preservation, based on which water absorption was calculated.

The flexural strength of the cured material was determined in the air at room temperature by the three-point support method (distance between leading points 20 mm, head speed 1 mm/min) by Instron strength testing machine. The results are shown in Table 2.

TABLE 2

| | | |
|---|---|---|
| Water absorption (%) | 1 week later | 0.08 |
| | 2 weeks later | 0.14 |
| Flexural strength (MPa) | immediately after preparation | 114.3 |
| | 1 week later | 116.3 |
| | 2 weeks later | 120.2 |

As is shown in Table 2, water absorption of the cured material was extremely small, and the mechanical strength of the cured material was retained even after immersion in physiological saline, whereby it has been clarified that the cured material has superior water resistance.

(Determination of heat generated during curing)

A chromel-almel thermocouple was fixed on the outside of 2.8 ml glass sample bottle. Equivalent amounts of the obtained paste (A1) and paste (B1) were placed in the sample bottle and mixed, and the maximum temperature reached by the heat generated during curing was measured.

As a result, the temperature reached 46° C. in 4.9 minutes from the initiation of the mixing.

(Effect of monomer (1))

Equivalent amounts of the obtained paste (A1) and paste (B1) were mixed. The obtained composition was interposed between two Teflon sheets and allowed to polymerize at room temperature for 10 minutes to give a plate-shaped cured material, which was immediately washed with water to remove the uncured layer on the surface.

Gold was deposited on the obtained plate-shaped cured material and the surface was observed in a scanning electron microscope. The results are shown in FIG. 1.

As is evident from FIG. 1, a number of hydroxyapatite particles (portions that look white in the photograph) were found on the surface of the obtained cured material.

(Effect of surface treatment of inorganic particles)

Equivalent amounts of the obtained paste (A1) and paste (B1) were mixed, and the mixture was allowed to cure to give a round rod having a diameter of 3 mm and a length of 28 mm, and a round rod having a diameter of 4 mm and a length of 4 mm.

The flexural strength of the former test sample was determined (the three-point support method, distance between leading points 20 mm, head speed 1 mm/min) by Instron strength testing machine, and the compressive strength of the latter test sample was determined (head speed 2 mm/min) by Instron strength testing machine in the air at room temperature (number of samples: 10, respectively).

The results revealed that the flexural strength was 118.1±10.6 MPa and the compressive strength was 239±13 MPa.

Comparative Example 1

Using commercially-available polymethyl methacrylate bone cement (polymerizable monomer content of the entire composition; 33% by weight), the temperature of the heat generated by curing was measured in the same manner as in Example 1.

As a result, the temperature reached 76.3° C. in 7.7 minutes from the initiation of the mixing of the powder agent and the liquid agent.

EXAMPLE 2

(Preparation of paste)

TEGDMA (50 parts by weight), Bis-MEPP (20 parts by weight) and Bis-GMA (30 parts by weight) were mixed, and benzoyl peroxide (0.3 part by weight) and hydroxyapatite powder (75 parts by weight) obtained in Reference Example 1 were added to this monomer mixture (25 parts by weight), which mixture was well admixed in a mortar to give a paste (A2). Separately, a monomer mixture (25 parts by weight) same as above was admixed with N,N-di(2-hydroxyethyl)-p-toluidine (0.5 part by weight) and hydroxyapatite powder (75 parts by weight) to give a paste (B2).

(Effect of inorganic powder content)

Equivalent amounts of the paste (A2) and paste (B2) were mixed, and placed in a brass mold to allow curing at room temperature. The mixture was allowed to stand overnight at 37° C. to give a round rod having a diameter of 4 mm and a thickness of 4 mm.

The obtained round rod was immersed in water at 70° C. for 24 hours, and water absorption was calculated from the weight thereof before and after the immersion. In the same manner as in Example 1, compressive strength in the air after immersion in water was determined (number of samples: 10).

The results are shown in Table 3.

Comparative Example 2

According to Japanese Patent Application under PCT laid-open under Kohyo No. 503148/1987, TEGDMA (50 parts by weight) and Bis-GMA (50 parts by weight) were mixed, and benzoyl peroxide (1 part by weight) and hydroxyapatite powder (70 parts by weight) were added to this monomer mixture (30 parts by weight), which mixture was well admixed in a mortar to give a paste (C). Separately, a monomer mixture (30 parts by weight) same as above was admixed with N,N-di(2-hydroxyethyl)-p-toluidine (0.6 part by weight) and hydroxyapatite powder (70 parts by weight) to give a paste (D).

Equivalent amounts of the paste (C) and paste (D) were mixed. In the same manner as in Example 2, round column specimens were prepared, and water absorption and compressive strength in the air after water absorption were determined (number of samples: 10).

The results are shown in Table 3.

TABLE 3

|  | Water absorption | Compressive strength after water absorption |
|---|---|---|
| Example 2 | 0.28 ± 0.09% | 178 ± 12 MPa |
| Comparative Example 2 | 0.69 ± 0.21% | 155 ± 11 MPa |

Table 3 shows significant difference of significance level of not more than 1% between Example 2 and Comparative Example 2 in water absorption and compressive strength after water absorption by the t-test.

Comparative Example 3

According to EP-B-123323, only Bis-MEPP was used as a monomer. Benzoyl peroxide (0.3 part by weight) and hydroxyapatite powder (80 parts by weight) were added to the monomer (20 parts by weight), which mixture was well admixed in a mortar to give a paste (E). Separately, a monomer (20 parts by weight) same as above was admixed with N,N-di(2-hydroxyethyl)-p-toluidine (0.5 part by weight) and hydroxyapatite powder (80 parts by weight) to give a paste (F).

Figure 2:
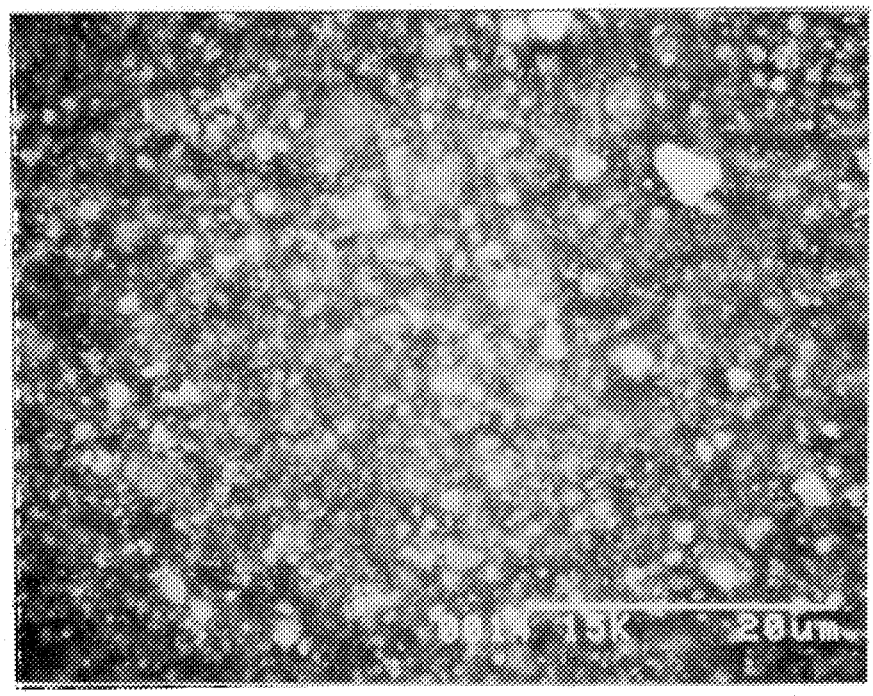
FIG. 2 is a surface electron microphotograph of a plate-shaped cured material obtained from the composition of Comparative Example 3.

Equivalent amounts of the paste (E) and paste (F) were admixed and a plate-shaped cured material was prepared in the same manner as in Example 1 (Effect of monomer (1)), and a surface electron microphotograph thereof was taken (FIG. 2). As is evident from FIG. 2, the cured material obtained from the composition of Comparative Example 3 without monomer (1) had a polymer membrane formed from a monomer on the hydroxyapatite particles.

Comparative Example 4

According to U.S. Pat. No. 4778834, hydroxyapatite (10 g) was stirred in an aqueous solution of sodium methasilicate 9 hydrate (0.5 g/70 ml, adjusted to pH 6.8 with 1N HCl) at room temperature overnight, washed, dried, and refluxed under heating for 3 hours in a solution (0.2 g/15 ml) of γ-methacryloxypropyl trimethoxysilane in toluene to give hydroxyapatite particles. In the same manner as in Example 1 except that the hydroxyapatite particles thus obtained were used, paste (G) and paste (H) were obtained.

Equivalent amounts of the obtained paste (G) and paste (H) were mixed and cured, and the flexural strength and compressive strength of the test samples were determined in the same manner as in Example 1 (Effect of surface treatment of inorganic particles) (number of samples: 10).

The results are shown in Table 4. The results of Example 1 are also shown for reference.

TABLE 4

|  | Flexural strength | Compressive strength |
|---|---|---|
| Example 1 | 118.1 ± 10.6 MPa | 239 ± 13 MPa |
| Comparative Example 4 | 89.6 ± 6.2 MPa | 210 ± 8 MPa |

There was found significant difference of significance level of not more than 1% between Example 4 and Comparative Example 3 in flexural strength and compressive strength by the t-test.

The consistency of the pastes of Example 1 and Comparative Example 4 was measured. That is, a glass plate weighing 40 g was placed on 0.5 ml of each paste, and the diameter of the paste was measured 30 seconds later. The results are shown in Table 5.

TABLE 5

|  | Consistency (mm) |
|---|---|
| Example 1 |  |
| paste (A1) | 23.5 |
| paste (B1) | 26.0 |
| Comparative Example 4 |  |
| paste (G) | 17.3 |
| paste (H) | 19.0 |

It has been recognized that the paste (A1) and paste (B1) of Example 1 are able to provide a restorative composition for hard tissue, which has a flowability suitable for extrusion from a dispenser.

Industrial Applicability

The restorative composition for hard tissue of the present invention shows high adhesion to bones and has sufficient water resistance. The heat generated by curing is small and gives minimal damage to the tissues of patients. In addition, the paste constituting the restorative composition for hard tissue has an adequate consistency, which facilitates homogeneous mixing of the pastes and application of the thereby-obtained mixture to the affected part by the use of a dispensing apparatus.

Therefore, the restorative composition for hard tissue of the present invention can be effectively used not only as a bone cement but also as a filler for the missing part of the bone, a bone prosthesis or an artificial bone.

What is claimed is:

1. A restorative composition for hard tissue, comprising a paste (A) comprising an inorganic calcium phosphate powder, a polymerizable monomer mixture and a polymerization initiator, and a paste (B) comprising an inorganic calcium phosphate powder, a polymerizable monomer mixture and a polymerization accelerator, wherein the content of the inorganic calcium phosphate powder in each paste is 75–85% by weight, and the above-mentioned polymerizable monomer mixtures each contain a monomer of the formula (I):

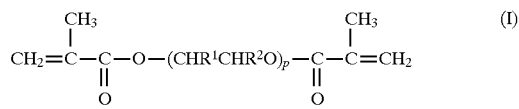

wherein $R^1$ and $R^2$ may be the same or different and each is a hydrogen atom or a methyl, and p is an integer of 1–4, and a monomer of the formula (2):

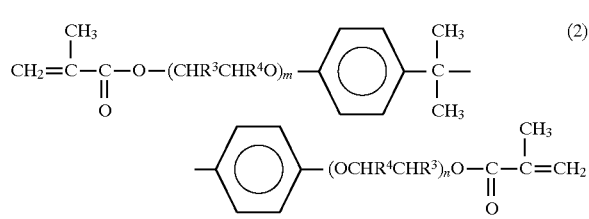

wherein $R^3$ and $R^4$ may be the same or different and each is a hydrogen atom or a methyl, m and n are each an integer of 1–5, and m+n is 2–6, the monomer of formula (1) being contained in a proportion of 40–65% by weight based on the total weight of the monomer mixtures wherein said paste (A) and said paste (B) each have a consistency in the range 20–27 mm and wherein the inorganic calcium phosphate powder has been subjected to primary treatment with an organic silane coupling agent, heat-treated at a temperature of 300°–800° C. and subjected to secondary treatment with an organic silane coupling agent.

2. The restorative composition for hard tissue of claim 1, wherein the monomer of the formula (1) is triethylene glycol dimethacrylate and the monomer of the formula (2) is 2,2-bis(4-methacryloxyethoxyphenyl)-propane.

3. A method for filling a cavity of hard tissue comprising placing separately the paste (A) and the paste (B) as defined in claim 1 into two containers of a dispensing apparatus, mixing homogeneously said two pastes by a static mixer mechanism of the dispensing apparatus and extruding the mixed paste to the cavity of hard tissue from the dispensing apparatus.

* * * * *